United States Patent
Tsunekawa et al.

(10) Patent No.: US 8,378,226 B2
(45) Date of Patent: Feb. 19, 2013

(54) WIRED CIRCUIT BOARD

(75) Inventors: Makoto Tsunekawa, Osaka (JP); Kei Nakamura, Osaka (JP); Takatoshi Sakakura, Osaka (JP); Yoshihiro Toyoda, Osaka (JP)

(73) Assignee: Nitto Denko Corporation, Osaka (JP)

( * ) Notice: Subject to any disclaimer, the term of this patent is extended or adjusted under 35 U.S.C. 154(b) by 827 days.

(21) Appl. No.: 12/285,600

(22) Filed: Oct. 9, 2008

(65) Prior Publication Data

US 2009/0114426 A1 May 7, 2009

(30) Foreign Application Priority Data

Nov. 6, 2007 (JP) ................................. 2007-288262

(51) Int. Cl.
*H05K 1/00* (2006.01)
*H01L 23/58* (2006.01)

(52) U.S. Cl. ......... 174/258; 174/250; 257/632; 257/642

(58) Field of Classification Search .................. 174/250, 174/258; 324/763.01; 29/825, 846
See application file for complete search history.

(56) References Cited

U.S. PATENT DOCUMENTS

| | | | | |
|---|---|---|---|---|
| 5,175,199 A * | 12/1992 | Asano et al. | ................... | 523/444 |
| 5,853,924 A * | 12/1998 | Uwami et al. | .................... | 430/7 |
| 5,892,241 A | 4/1999 | Moriya | | |
| 6,900,989 B2 * | 5/2005 | Sakata | .......................... | 361/749 |
| 7,173,322 B2 * | 2/2007 | Sakata et al. | ................... | 257/678 |
| 7,198,989 B2 * | 4/2007 | Sakata et al. | ................... | 438/117 |
| 7,255,919 B2 * | 8/2007 | Sakata et al. | ................... | 428/352 |
| 7,312,104 B2 * | 12/2007 | Noro | ............................. | 438/108 |
| 7,382,042 B2 * | 6/2008 | Awata et al. | ................... | 257/643 |
| 7,649,310 B2 * | 1/2010 | Ishii et al. | ...................... | 313/503 |
| 7,777,835 B2 * | 8/2010 | Park et al. | ......................... | 349/69 |
| 2005/0132387 A1 * | 6/2005 | Katayama et al. | ............. | 720/600 |
| 2006/0019077 A1 | 1/2006 | Hopper et al. | | |
| 2007/0285539 A1 * | 12/2007 | Shimizu et al. | ............... | 348/272 |
| 2009/0113701 A1 * | 5/2009 | Toyoda | ........................... | 29/825 |
| 2009/0113704 A1 * | 5/2009 | Toyoda | ........................... | 29/850 |
| 2010/0201802 A1 * | 8/2010 | Onishi et al. | .................... | 348/87 |
| 2010/0208250 A1 * | 8/2010 | Ihara et al. | ................. | 356/237.4 |
| 2010/0263206 A1 * | 10/2010 | Toyoda et al. | .................. | 29/829 |

FOREIGN PATENT DOCUMENTS

| | | |
|---|---|---|
| EP | 0 138 209 | 4/1985 |
| EP | 0 282 638 | 9/1988 |
| EP | 0 385 474 | 9/1990 |
| EP | 0 891 127 | 1/1999 |
| EP | 2 056 097 | 5/2009 |

(Continued)

OTHER PUBLICATIONS

Photonic Multichannel Spectral Analyzer Model: PMA-11, Hamamatsu Photonics K. K., 2001.*

(Continued)

*Primary Examiner* — Jayprakash N Gandhi
*Assistant Examiner* — Dion Ferguson
(74) *Attorney, Agent, or Firm* — Jean C. Edwards, Esq.; Edwards Neils PLLC

(57) ABSTRACT

A wired circuit board includes a conductive pattern, and an insulating layer covering the conductive pattern and having a transmittance of not more than 30% with respect to a wavelength in a range of 600 to 680 nm.

1 Claim, 2 Drawing Sheets

FOREIGN PATENT DOCUMENTS

| | | |
|---|---|---|
| JP | 08-181421 | 7/1996 |
| JP | 10160928 A * | 6/1998 |
| JP | 2001-281165 | 10/2001 |
| JP | 2002-296016 | 10/2002 |
| JP | 2005-283583 | 10/2005 |
| JP | 2006112845 A * | 4/2006 |
| WO | WO 2006068141 A1 * | 6/2006 |
| WO | WO 2009/011337 | 1/2009 |

OTHER PUBLICATIONS

Transmission of Wratten Filters, Complied by Allie C. Peed, CRC Handbook of Chemistry and Physics, 64th ed., pp. E-394 to E-401, 1983.*

Transmission of Wratten Filters, Complied by Allie C. Peed, CRC Handbook of Chemistry and Physics, $64^{th}$ ed., pp. E-394 to E-401 [NO DATE].*

* cited by examiner

WIRED CIRCUIT BOARD

CROSS-REFERENCE TO RELATED APPLICATION

The present application claims priority from Japanese Patent Application No. 2007-288262 filed on Nov. 6, 2007, the content of which is herein incorporated by reference in its entirety.

BACKGROUND OF THE INVENTION

1. Field of the Invention

The present invention relates to a wired circuit board and, more particularly, to a wired circuit board such as a chip on film (COF) board or a flexible wired circuit board.

2. Description of the Related Art

A wired circuit board such as a COF board or a flexible wired circuit board includes an insulating base layer, a conductive pattern formed thereon, and an insulating cover layer formed on the insulating base layer so as to cover the conductive pattern. Such a wired circuit board is widely used in the field of various electric equipment and electronic equipment.

For such a wired circuit board, it has been proposed to, e.g., emit a light beam toward a wired circuit board, and measure the reflected light or transmitted light thereof so as to sense a foreign matter or the displacement of a conductive pattern or an insulating cover layer, and sense a defect in the wired circuit board (see, e.g., Japanese Unexamined Patent No. 2005-283583).

SUMMARY OF THE INVENTION

In the wired circuit board proposed in Japanese Unexamined Patent No. 2005-283583, when the insulating cover layer is formed with a relatively small thickness (e.g., not more than 5 μm), such a conductive pattern may be erroneously determined (erroneous sensing) as a foreign matter in accordance with the reflected light based on the conductive pattern.

When the conductive pattern is formed by a subtractive method, the surface of the conductive pattern may be roundly formed in a slightly curved shape by over-etching a conductive layer exposed from an etching resist. In that case, it is necessary to increase the amount of the emitted light beam in an inspection so that there also may be erroneous sensing in the same manner as described above.

It is therefore an object of the present invention to provide a wired circuit board which allows the prevention of erroneous sensing in a foreign matter inspection, or in an inspection of a conductive pattern or an insulating cover layer.

A wired circuit board of the present invention includes a conductive pattern, and an insulating layer covering the conductive pattern and having a transmittance of not more than 30% with respect to a wavelength in a range of 600 to 680 nm.

Further, a wired circuit board of the present invention includes a conductive pattern, and an insulating layer covering the conductive pattern and having a transmittance of not less than 55% with respect to a wavelength in a range of 500 to 580 nm.

Still further, a wired circuit board of the present invention includes a conductive pattern, and an insulating layer covering the conductive pattern, and having a transmittance of not more than 30% with respect to a wavelength in a range of 600 to 680 nm and a transmittance of not less than 55% with respect to a wavelength in a range of 500 to 580 nm.

In the wired circuit board of the present invention, the transmittance of the insulating layer with respect to a specified wavelength is not more than a specified value. Accordingly, in a foreign matter inspection, it is possible to prevent the erroneous sensing of the conductive pattern as a foreign matter. Additionally, in an inspection of the insulating layer, it is possible to correctly recognize the shape of the insulating layer, and precisely sense a shape defect in the insulating layer or the like.

In the wired circuit board of the present invention, the transmittance of the insulating layer with respect to a specified wavelength is not less than a specified value. Accordingly, in an inspection of the conductive pattern, it is possible to correctly recognize the shape of the conductive pattern, and precisely determine the presence of a defect in the conductive pattern or the like.

DETAILED DESCRIPTION OF THE INVENTION

Figure 1:
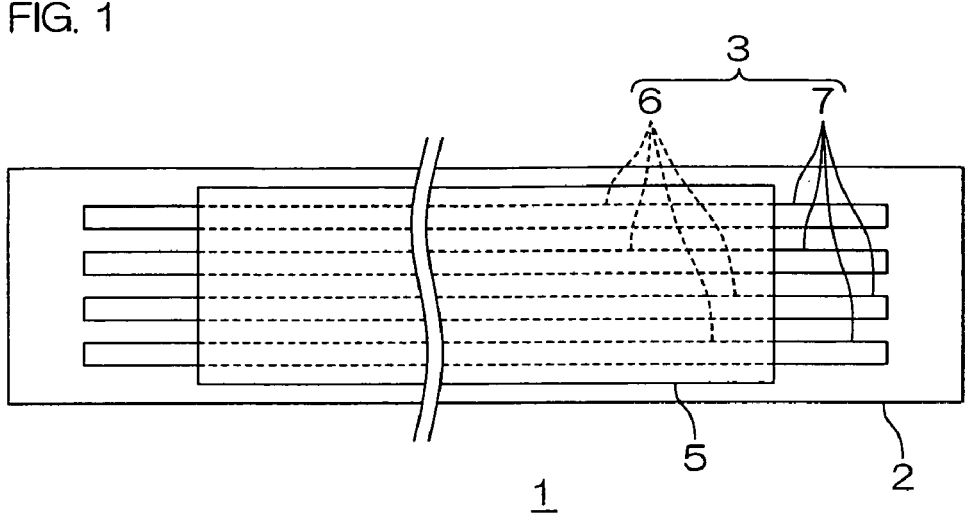
FIG. 1 is a plan view of a wired circuit board according to an embodiment of the present invention.
Figure 2:
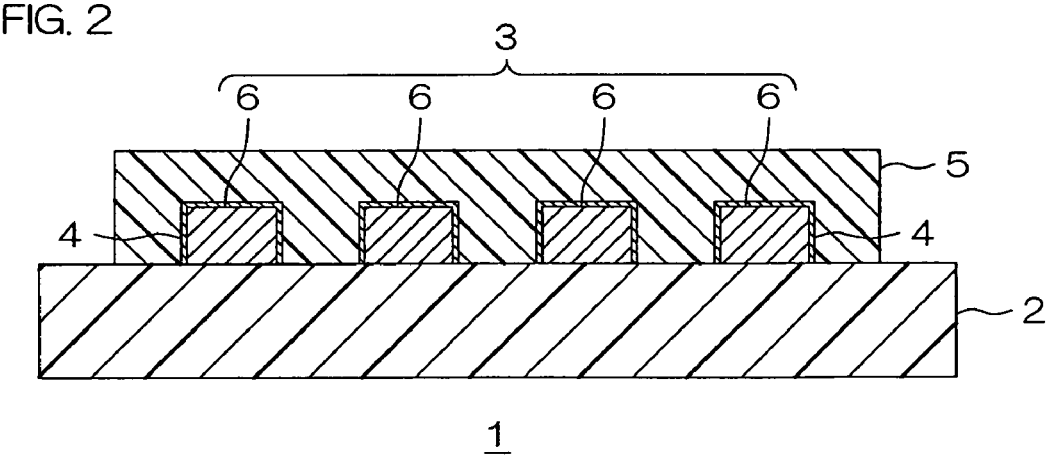
FIG. 2 is a cross-sectional view of the wired circuit board shown in FIG. 1 along a widthwise direction.
Figure 3:
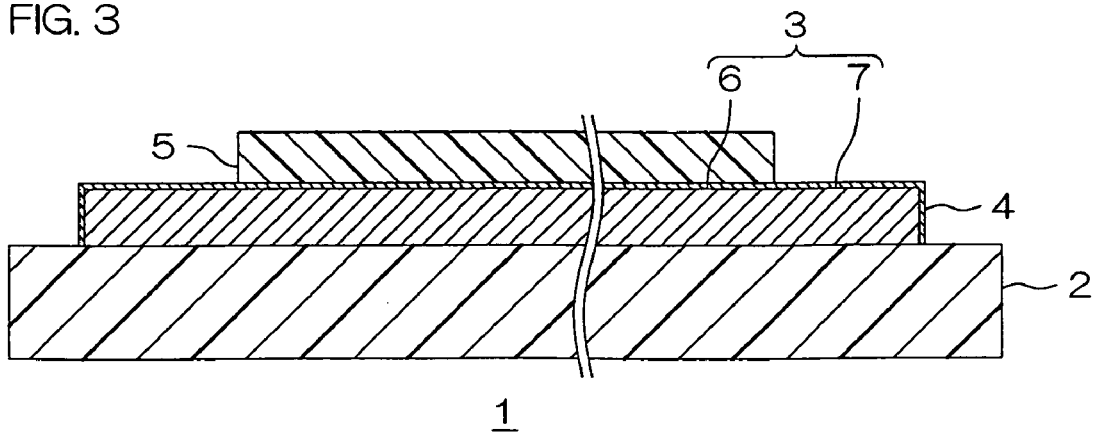
FIG. 3 is a partial cross-sectional view of the wired circuit board shown in FIG. 1 along a longitudinal direction.

FIG. 1 is a plan view of a wired circuit board according to an embodiment of the present invention. FIG. 2 is a cross-sectional view of the wired circuit board shown in FIG. 1 along a widthwise direction (perpendicular to a longitudinal direction). FIG. 3 is a partial cross-sectional view of the wired circuit board shown in FIG. 1 along the longitudinal direction. In FIG. 1, a metal thin film 4 described later is omitted for clear illustration of relative positioning of a conductive pattern 3.

In FIG. 1, a wired circuit board 1 is a flexible wired circuit board formed in a flat belt shape extending in the longitudinal direction. As shown in FIGS. 2 and 3, the wired circuit board 1 includes an insulating base layer 2, the conductive pattern 3 formed on the insulating base layer 2, and an insulating cover layer 5 as an insulating layer formed on the insulating base layer 2 so as to cover the conductive pattern 3.

Examples of an insulating material used to form the insulating base layer 2 include synthetic resins such as a polyimide resin, a polyamide imide resin, an acrylic resin, a polyether nitrile resin, a polyether sulfone resin, a polyethylene terephthalate resin, a polyethylene naphthalate resin, and a polyvinyl chloride resin. Preferably, a polyimide resin is used in terms of heat resistance and chemical resistance.

The insulating base layer 2 is formed in a flat belt shape in correspondence to the outer shape of the wired circuit board 1 extending in the longitudinal direction. The thickness of the insulating base layer 2 is in a range of, e.g., 5 to 50 μm, or preferably 10 to 40 μm.

Examples of a conductive material used to form the conductive pattern 3 include, e.g., copper, nickel, gold, a solder, and an alloy thereof. Preferably, copper is used in terms of electric resistance.

As shown in FIGS. 1 and 3, the conductive pattern 3 integrally includes wires 6 extending along the longitudinal direction, and arranged in parallel and mutually spaced-apart relation in the widthwise direction, and terminal portions 7 disposed at the both longitudinal end portions of the respective wires 6. Each of the wires 6 is covered with an insulating cover layer 5, while each of the terminal portions 7 is exposed from the insulating cover layer 5. As shown in FIG. 2, the conductive pattern 3 is formed in a generally rectangular shape in a cross section along the widthwise direction.

The thickness of the conductive pattern 3 is in a range of, e.g., 3 to 30 μm, or preferably 5 to 20 μm. The respective widths (widthwise lengths) of the wires 6 and the terminal portions 7 may be the same or different, and are in a range of, e.g., 5 to 500 μm, or preferably 15 to 200 μm. The respective distances (widthwise spacings) between the individual wires 6 and between the individual terminal portions 7 may be the same or different, and are in a range of, e.g., 5 to 200 μm, or preferably 5 to 100 μm.

The insulating cover layer 5 covers and electrically seals the wires 6. As an insulating material for forming the insulating cover layer 5, the same insulating material is used as the insulating material for forming the insulating base layer 2 mentioned above, or a resin material such as a solder resist. In the insulating material mentioned above, a pigment or the like is preferably mixed.

The pigment is mixed as necessary to facilitate an inspection of the insulating cover layer 5 described later. For example, an organic pigment is used. Examples of the organic pigment to be used include a green pigment, a blue pigment, a yellow pigment, and a red pigment. Preferably, a green pigment is used. As the green pigment, phthalocyanine green, iodine green, or the like is used. Examples of the green pigment include a pigment mixture of a blue pigment and a yellow pigment. For example, a pigment mixture of phthalocyanine blue and disazo yellow is used. These pigments can be used alone or in combination.

The ratio of the pigment contained in the insulating cover layer 5 is, e.g., not less than 0.2 wt %, or preferably not less than 0.4 wt %, and, e.g., not more than 2.5 wt %, or preferably, not more than 1.5 wt %. When the mixture ratio of the pigment (e.g., a green pigment) is within the range shown above, the transmittance of the insulating cover layer 5 with respect to a wavelength in a range of 600 to 680 nm and/or a wavelength in a range of 500 to 580 nm, which is described later, can be set to a predetermined range.

The insulating cover layer 5 is formed on the insulating base layer 2 so as to cover the wires 6 and expose the terminal portions 7. More specifically, the insulating cover layer 5 is formed in a flat belt shape which is slightly shorter than the insulating base layer 2 in the longitudinal direction, as shown in FIGS. 1 and 3.

The transmittance of the insulating cover layer 5 with respect to a wavelength in the range of 600 to 680 nm is not more than 30%, preferably not more than 25%, or more preferably not more than 20%, and normally not less than 10%. When the transmittance with respect to a wavelength in the range of 600 to 680 nm is not more than 30%, erroneous sensing of the conductive pattern can be prevented in a foreign matter inspection using a light beam at a wavelength in the range of 600 to 680 nm. Alternatively, in a shape recognition inspection (described later) of the insulating cover layer 5 using a light beam at a wavelength in the range of 600 to 680 nm, the shape of the insulating cover layer 5 can be correctly recognized.

The transmittance of the insulating cover layer 5 with respect to a wavelength in the range of 500 to 580 nm is not less than 55%, preferably not less than 65%, or more preferably not less than 70%, and normally not more than 95%. When the transmittance with respect to a wavelength in the range of 500 to 580 nm is not less than 55%, the shape of the conductive pattern 3 can be correctly recognized in a shape recognition inspection of the conductive pattern 3 using a light beam at a wavelength in the range of 500 to 580 nm.

The thickness of the insulating cover layer 5 is, e.g., not less than 5 μm, or preferably not less than 7 μm, and, e.g., not more than 15 μm, or preferably not more than 12 μm.

When the thickness of the insulating cover layer 5 is not less than the lower limit shown above, the transmittance of the insulating cover layer 5 with respect to a wavelength in the range of 600 to 680 nm can be set to the range (e.g., not more than 30%) shown above. When the thickness of the insulating cover layer 5 is not more than the upper limit shown above, the transmittance of the insulating cover layer 5 with respect to a wavelength in the range of 500 to 580 nm can be set to the range (e.g., not less than 55%) shown above.

Additionally, as shown in FIGS. 2 and 3, the metal thin film 4 is provided as necessary on the surface of the conductive pattern 3. In this case, i.e., the metal thin film 4 is interposed between the conductive pattern 3 and the insulating cover layer 5. Examples of a metal material for forming the metal thin film 4 include metals such as tin, nickel, gold, chromium, titanium, zirconium, and an alloy thereof. Preferably, tin is used. The thickness of the metal thin film 4 is in a range of, e.g., 0.2 to 5 μm, or preferably 0.5 to 2 μm.

Next, a description is given to a producing method of the wired circuit board 1.

First, the insulating base layer 2 is prepared in the method. The insulating base layer 2 is preliminarily prepared as a film of a synthetic resin, or by coating a varnish of a synthetic resin on a release plate (e.g., a release plate made of a metal such as stainless steel) not shown, drying the varnish of the synthetic resin, and then curing it as necessary. Alternatively, the insulating base layer 2 is prepared by coating a varnish of a photosensitive synthetic resin on a release plate, drying the varnish, developing it, processing it into the foregoing pattern, and then curing it as necessary.

Next, the conductive pattern 3 is formed as a wired circuit pattern having the wires 6 and the terminal portions 7 on the insulating base layer 2. The conductive pattern 3 is formed by a known patterning method such as, e.g., a subtractive method or an additive method.

Next, the metal thin film 4 is formed on the surface of the conductive pattern 3 including the wires 6. The metal thin film 4 is laminated by plating such as, e.g., electroless plating.

Next, in the method, the insulating-cover layer 5 is formed in the foregoing pattern on the insulating base layer 2 so as to cover the metal thin film 4.

The insulating cover layer 5 is formed by a known method such as, e.g., the coating of a resin solution containing a pigment as necessary, or the bonding of a resin film containing a pigment as necessary.

In the coating of a resin solution, when the resin solution contains a pigment, a resin solution (varnish) is prepared first by mixing a solution of the synthetic resin mentioned above and the pigment. A solvent for forming the varnish is not particularly limited as long as the synthetic resin and the pigment can be dispersed (dissolved) therein. For example, an organic solvent such as N-methyl-2-pyrollidone (NMP) or Carbitol acetate is used. In the solution of the synthetic resin, the mixture ratio of the synthetic resin to 100 parts by weight of the synthetic resin solution is in a range of, e.g., 38 to 42 parts by weight. The mixture ratio of the pigment to the varnish is set to correspond to the ratio of the pigment contained in the insulating cover layer 5 mentioned above.

Next, the varnish is coated on the insulating base layer 2 and the metal thin film 4 to form a cover coating. For the coating of the varnish, a coating method such as, e.g., screen printing is used. Thereafter, the formed cover coating is dried by heating at 100 to 150° C. for 30 to 90 minutes to form the cover coating.

It is also possible to cause the resin solution to further contain a photosensitive agent, and form the insulating cover layer 5 in the foregoing pattern by photoprocessing.

The insulating cover layer 5 can be formed by photoprocessing as follows. For example, a varnish containing a pigment and a photosensitive agent (a varnish of a photosensitive synthetic resin and a pigment) is coated on the entire surface of the insulating base layer 2 including the metal thin film 4 by a coating method such casting, and dried to form a cover coating. Then, the cover coating is exposed to light via a photomask, developed, processed into a pattern, and then cured as necessary to form the insulating cover layer 5.

In the bonding of the resin film, a film of the insulating material (containing a pigment as necessary) preliminarily formed in the foregoing pattern is laminated on the insulating base layer 2 and the metal thin film 4 via a known adhesive.

In this manner, the insulating cover layer 5 is formed, and then the wired circuit board 1 is formed.

Next, an inspection of the wired circuit board 1 will be described with reference to FIGS. 4 and 5.

The inspection of the wired circuit board 1 is performed by an optical inspection with respect to the wired circuit board 1 after the production thereof or the wired circuit board in the process of the production thereof.

Specifically, a light beam at a wavelength in the range of 600 to 680 nm is used in the optical inspection. When the wavelength of the light beam is within the range shown above, it is possible to prevent erroneous sensing of the conductive pattern 3, and to achieve normal recognition of the insulating cover layer 5 in the case where the insulating cover layer 5 containing a pigment (e.g., a green pigment) is formed. Such a light beam can be used, e.g., as single wavelength light, as multiple wavelength light at two or more different wavelengths, or as continuous wavelength light within the range shown above.

Figure 4:
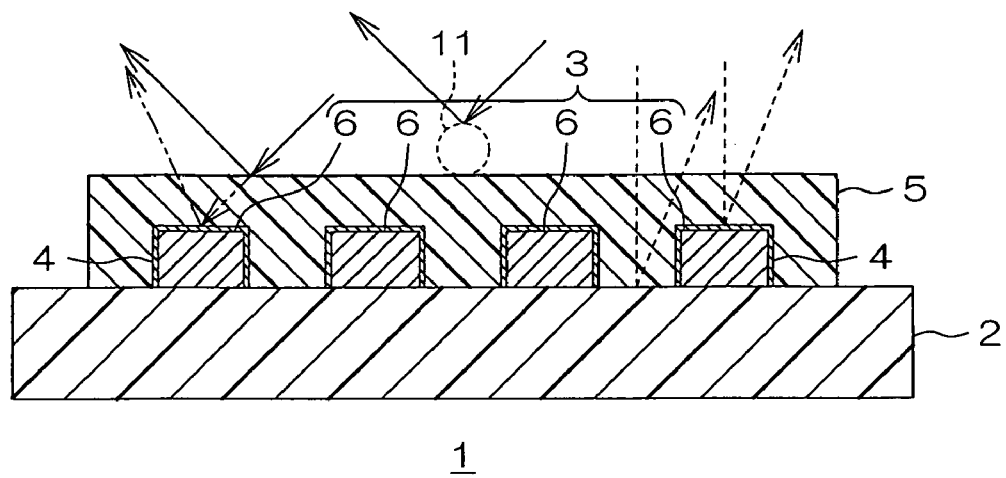
FIG. 4 is a view for illustrating an optical inspection of the wired circuit board, which is a cross-sectional view of the wired circuit board along the widthwise direction.

For the inspection, a sensor device not shown and including a light emitting unit not shown and a light receiving unit not shown is disposed to face the insulating cover layer 5 including the conductive pattern 3, as shown in FIG. 4. The light emitting unit is capable of emitting a light beam at the wavelength shown above to a point above the conductive pattern 3 and the insulating cover layer 5 in the wired circuit board 1 in the process of the production thereof or after the production thereof.

Next, a light beam (at 600 to 680 nm) is emitted from the light emitting unit toward the insulating cover layer 5 including the wires 6 to sense the light (solid line) reflected by the upper surface of the insulating cover layer 5 or the light (solid line) reflected by the surface of a foreign matter 11 (broken-line circle) remaining on the upper surface of the insulating cover layer 5. As a result, it is possible to precisely determine the presence of the foreign matter 11 on the upper surface of the insulating cover layer 5.

As the foreign matter 11, a metal foreign matter resulting from the production of the wired circuit board 1, and from the conductive pattern 3, the metal thin film 4, the release plate, or the like can be listed. Specifically copper, tin, stainless steel, or the like can be listed respectively.

Specifically, in an inspection for the foreign matter 11, when the reflected light from the foreign matter 11 is obtained as pattern data which is not present in the original pattern data of the conductive pattern 3, it is determined that the foreign matter 11 is present on the insulating cover layer 5 based on the pattern data of the conductive pattern 3 preliminarily obtained in an inspection of the conductive pattern 3 described later. On the other hand, when there is no difference between the preliminarily obtained pattern data of the conductive pattern 3 and the original pattern data of the conductive pattern 3, it is determined that the foreign matter 11 is not present on the insulating cover layer 5.

In particular, since the transmittance of the insulating cover layer 5 with respect to a light beam at a wavelength in the range of 600 to 680 nm is not more than 30%, the light beam which passes through the upper surface of the insulating cover layer 5 is downwardly transmitted through the interior of the insulating cover layer 5, reflected by the upper surface of the metal thin film 4, and further upwardly transmitted through the interior of the insulating cover layer 5 to upwardly pass through the upper surface of the insulating cover layer 5, as indicated by the imaginary line in FIG. 4. Accordingly, the transmitted light is sufficiently absorbed by the insulating cover layer 5, and sufficiently reduced in intensity so that it is prevented from being erroneously sensed as the reflected light from the foreign matter 11.

Figure 5:
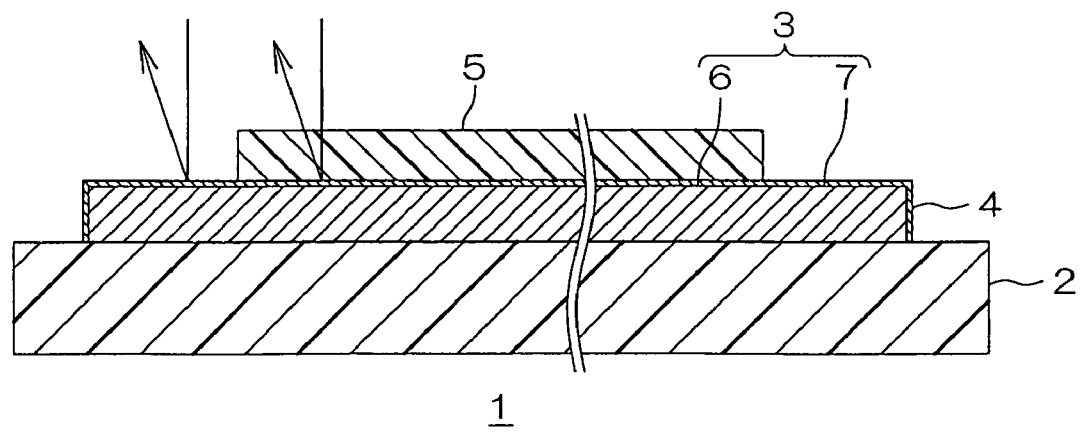
FIG. 5 is a view for illustrating an optical inspection of the wired circuit board, which is a partial cross-sectional view of the wired circuit board along the longitudinal direction.

At the same time, as shown in FIG. 5, a light beam is emitted from the light emitting unit toward the terminal portion 7 and the insulating cover layer 5 in the vicinity thereof, and the light reflected by the lower surface (upper surface of the metal thin film 4) of the insulating cover layer 5, and the light reflected by the upper surface (upper surface of the metal thin film 4) of the terminal portion 7 are sensed. As a result, it is possible to correctly recognize the shape of the insulating cover layer 5, i.e., the positions of the both longitudinal end edges of the insulating cover layer 5, and precisely determine a shape defect in the insulating cover layer 5 (e.g., a shape defect in the insulating cover layer 5 not exposing, but covering the terminal portion 7). In other words, the shape of the terminal portion 7 exposed from the insulating cover layer 5 along the longitudinal direction can be precisely determined.

For the optical inspection, a light beam at a different wavelength can also be used in addition to or instead of the light beam at a wavelength in the range of 600 to 680 nm shown above.

As such a light beam for the optical inspection, a light beam at a wavelength in the range of 500 to 580 nm is used. Such a light beam can be used, e.g., as single wavelength light, as multiple wavelength light at two or more different wavelengths, or as continuous wavelength light within the range shown above.

Then, as shown in FIG. 4, the light beam (at 500 to 580 nm) is emitted from the light emitting unit toward the insulating cover layer 5 including the wires 6 to sense the light (in broken line) reflected by the surface of the metal thin film 4 covered with the insulating cover layer 5 at the lower surface of the insulating cover layer 5, i.e., the surface of the wire 6, and the light (in broken line) reflected by the surface of the insulating base layer 2 covered with the insulating cover layer 5. As a result, it is possible to obtain the pattern data of the conductive pattern 3, correctly recognize the shape of the conductive pattern 3, and precisely determine a defect in the wire 6, a short circuit between the wires 6, or the like.

In particular, since the transmittance of the insulating cover layer 5 with respect to a light beam at a wavelength in the range of 500 to 580 nm is not less than 55%, the difference between the respective intensities of the light reflected by the surface of the metal thin film 4 and the light reflected by the surface of the insulating base layer 2 can be easily and distinctly recognized, and the shape of the conductive pattern 3 can be correctly recognized.

In the description given above, the flexible wired circuit board in which the insulating base layer 2 is not supported is shown as an example of the wired circuit board of the present invention. However, the wired circuit board of the present invention is also widely applicable to various flexible wired circuit boards such as, e.g., a flexible wired circuit board in which a metal support layer is provided as a reinforcing layer to support the lower surface of the insulating base layer 2, and a COF board (including a TAB tape carrier or the like), though not shown.

EXAMPLES

Example 1

Production of Flexible Wired Circuit Boards Nos. 1 to 5

An insulating base layer made of a film of a polyimide resin having a thickness of 35 μm was prepared. Then, a conductive pattern having a thickness of 8 μm was formed in a wired circuit pattern having wires and terminal portions on the insulating base layer by an additive method. Then, a metal thin film made of tin and having a thickness of 0.5 μm was formed on the surface of the conductive pattern by electroless tin plating.

Then, an insulating cover layer was formed on the insulating base layer so as to cover the metal thin film. In the formation of the insulating cover layer, 40 parts by weight of an acrylic resin, 35 parts by weight of Carbitol acetate, and 3 parts by weight of NMP were mixed first, and then 7.2 parts by weight of a green pigment (phthalocyanine green, UTCO-061: commercially available from Dainichiseika Color & Chemicals Mfg. Co., Ltd.) was further mixed to prepare a varnish of an acrylic resin. Then, the prepared varnish was coated in the foregoing pattern on the insulating base layer and the metal thin film by screen printing. Thereafter, the varnish was dried by heating at 150° C. for 30 minutes to form an insulating cover layer having a thickness of 10 μm. The ratio of the pigment contained in the insulating cover layer was 0.5 wt %. In this manner, a flexible wired circuit board was obtained as the sample No. 1 (see FIGS. 2 and 3).

Subsequently, in accordance with the sample No. 1, flexible wired circuit boards Nos. 2 to 5 were obtained by varying the amount of the pigment mixed in the varnish, as shown in Table 1, in the formation of the insulating cover layer.

Example 2

Production of Flexible Wired Circuit Boards Nos. 6 to 12

Flexible wired circuit boards Nos. 6 to 12 were obtained in the same manner as in Example 1 except that the amount of the pigment mixed in the varnish was varied, and the thickness of the insulating cover layer was changed from 10 μm to 5 μm as shown in Table 2.

Example 3

Production of Flexible Wired Circuit Boards Nos. 13 to 20

Flexible wired circuit boards Nos. 13 to 20 were obtained in the same manner as in Example 1 except that, in the preparation of the varnish in the formation of the insulating cover layer, the amount of the mixed pigment was changed to 4.8 parts by weight, and the thickness of the insulating cover layer was set as shown in Table 3.

(Evaluation)

(1) Measurement of Transmittance

Insulating cover layers which were the same as the insulating cover layers of the flexible wired circuit boards Nos. 1 to 20 were formed individually on polyethylene terephthalate plates each having a thickness of 50 μm by the same method as described above. Then, the transmittances of each of the insulating cover layers with respect to the wavelengths of 640 nm and 530 nm were measured using a transmittance measuring device (Photal, MULTI CHANNEL PHOTO DETECTOR in a transmittance measurement mode: commercially available from Otsuka Electronics Co., Ltd.). The results of the measurement are shown in Tables 1 to 3.

(2) Foreign Matter Inspection Test

With respect to each of the flexible wired circuit boards Nos. 1 to 20, a foreign matter inspection test for determining whether or not a foreign matter remained on the surface of the insulating cover layer was performed one hundred times. The foreign matter inspection test was performed using a light beam at a wavelength of 640 nm in a sensor device (AVS-5500: commercially available from Ajuhitek Inc.) including a light emitting unit (light source) and a light receiving unit (CCD camera). The results of the foreign matter inspection tests are shown in Tables 1 to 3. Each of the values in Tables 1 to 3 shows the rate at which a foreign matter was erroneously sensed (i.e., the conductive pattern was erroneously sensed as a foreign matter) even though no foreign matter was actually on the surface of the insulating base layer in the foreign matter inspection test.

(3) Shape Recognition Inspection of Conductive Pattern

With respect to each of the flexible wired circuit boards Nos. 1 to 20, a shape recognition inspection of the conductive pattern was performed. The shape recognition inspection was performed using a light beam at a wavelength of 530 nm in the same sensor device (AVS-5500: commercially available from Ajuhitek Inc.) as mentioned above. The results of the shape recognition inspections are shown in Tables 1 to 3. In Table 3, the word "Error" indicates that a defect was erroneously sensed (erroneous sensing) even though no defect was actually formed in the conductive pattern in the shape recognition inspection, and the word "Normal" indicates that the conductive pattern was sensed as normal. The results of the sensing are shown in Tables 1 to 3.

TABLE 1

(Thickness of Insulating Cover Layer: 10 μm)

| Sample No. | Amount of Pigment Mixed in 100 Parts by Weight of Varnish (Parts by Weight) | Light Beam at Wavelength of 640 nm | | Light Beam at Wavelength of 530 nm | |
|---|---|---|---|---|---|
| | | Transmittance (%) | Frequency of Erroneous Sensing of Foreign Matter (%) | Transmittance (%) | Shape Recognition of Conductive Pattern |
| 1 | 7.2 | 12.5 | 0 | 71.8 | "Normal" |
| 2 | 4.8 | 24.0 | 0 | 74.6 | "Normal" |
| 3 | 2.4 | 45.1 | 87 | 77.4 | "Normal" |
| 4 | 1.2 | 61.7 | 100 | 79.1 | "Normal" |
| 5 | 0 | 83.0 | 100 | 78.9 | "Normal" |

TABLE 2

(Thickness of Insulating Cover Layer: 5 μm)

| Sample No. | Amount of Pigment Mixed in 100 Parts by Weight of Varnish (Parts by Weight) | Light Beam at Wavelength of 640 nm | | Light Beam at Wavelength of 530 nm | |
|---|---|---|---|---|---|
| | | Transmittance (%) | Frequency of Erroneous Sensing of Foreign Matter (%) | Transmittance (%) | Shape Recognition of Conductive Pattern |
| 6 | 12.0 | 18.4 | 0 | 75.8 | "Normal" |
| 7 | 9.6 | 25.5 | 0 | 75.2 | "Normal" |
| 8 | 7.2 | 32.7 | 32 | 77.8 | "Normal" |
| 9 | 4.8 | 43.5 | 78 | 78.6 | "Normal" |
| 10 | 2.4 | 61.3 | 100 | 78.7 | "Normal" |
| 11 | 1.2 | 76.2 | 100 | 79.0 | "Normal" |
| 12 | 0 | 83.0 | 100 | 78.9 | "Normal" |

TABLE 3

(Amount of Pigment Mixed in 100 Parts by Weight of Varnish: 4.8 Parts by Weight)

| Sample No. | Thickness of Insulating Cover Layer (μm) | Light Beam at Wavelength of 640 nm | | Light Beam at Wavelength of 530 nm | |
|---|---|---|---|---|---|
| | | Transmittance (%) | Frequency of Erroneous Sensing of Foreign Matter (%) | Transmittance (%) | Shape Recognition of Conductive Pattern |
| 13 | 10 | 37.4 | 78 | 75.7 | "Normal" |
| 14 | 12.5 | 29.7 | 0 | 74.1 | "Normal" |
| 15 | 15 | 21.9 | 0 | 72.9 | "Normal" |
| 16 | 20 | 16.3 | 0 | 68.0 | "Normal" |
| 17 | 25 | 10.3 | 0 | 64.9 | "Normal" |
| 18 | 30 | 7.4 | 0 | 62.7 | "Normal" |
| 19 | 40 | 3.5 | 0 | 57.1 | "Normal" |
| 20 | 50 | 1.4 | 0 | 48.7 | "Error" |

While the illustrative embodiments of the present invention are provided in the above description, such is for illustrative purpose only and it is not to be construed limitative. Modification and variation of the present invention that will be obvious to those skilled in the art is to be covered by the following claims.

What is claimed is:
1. A wired circuit board comprising:
a conductive pattern made of copper and formed in a wired circuit pattern having wires and terminal portions; and
an insulating layer covering the conductive pattern, the insulating layer comprising a synthetic resin and a pigment, and having a transmittance of not more than 30% as measured using light at a wavelength in a range of 600 to 680 nm passing through the insulating layer only once by a multi-channel photo detector in a transmittance measurement mode, and having a transmittance of not less than 55% as measured with light at a wavelength in a range of 500 to 580 nm passing through the insulating layer only once by a multi-channel photo detector in a transmittance measurement mode.

* * * * *